United States Patent [19]

Trinn et al.

[11] Patent Number: 4,618,581

[45] Date of Patent: Oct. 21, 1986

[54] CLAVINE-PRODUCING STRAIN, A PROCESS FOR THE PREPARATION THEREOF AS WELL AS A MICROBIOLOGICAL PROCESS FOR PRODUCING CLAVINE ALKALOIDS

[75] Inventors: Mária Trinn, Pecs; Gabriella Kordik, Budapest; Eva Udvardy-Nagy née Cserey Pecháany, Budapest; Zsuzsanna Vida, Budapest; Rzsebet Zsóka née Sómkuti, Budapest, all of Hungary

[73] Assignee: Richter Gedeon Vegyeszeti Gyar RT., Budapest, Hungary

[21] Appl. No.: 637,524

[22] Filed: Aug. 3, 1984

[30] Foreign Application Priority Data

Aug. 10, 1983 [HU] Hungary ........................ 2817/83

[51] Int. Cl.[4] ...................... C12P 17/18; C12N 15/00; C12N 1/14

[52] U.S. Cl. ................................ 435/119; 435/172.1; 435/254

[58] Field of Search ...................... 435/119, 172.1, 254

[56] References Cited

U.S. PATENT DOCUMENTS 3,884,762 5/1975 Wack et al. ........................ 435/119

OTHER PUBLICATIONS

Turner et al., Fungal Metabolites II, Academic Press, p. 400, (1983).

*Primary Examiner*—Alvin E. Tanenholtz

*Attorney, Agent, or Firm*—Karl F. Ross; Herbert Dubno

[57] ABSTRACT

The invention relates to a new microbiological process for the preparation of clavine alkaloids of the general formula (I),

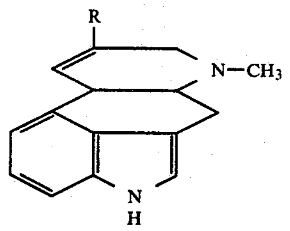

(I)

wherein R stands for hydroxymethyl or methyl group, by cultivation of a *Claviceps fusiformis* strain in liquid submerged culture medium containing sources of carbon, nitrogen, mineral salts and optionally other additives, under aerobic conditions, in which a *Claviceps fusiformis* variant strain deposited under No. 00211 is used as alkaloid-producing strain. The invention further relates to a biologically pure culture of the *Claviceps fusiformis* variant strain No. 00211 obtained in a process in which a *Claviceps fusiformis* strain No. 00164 is grown in a solid culture medium containing sources of carbon, nitrogen, mineral salts and agar as well as an additive promoting the formation of cytochrome P-450, followed by the selective isolation of the new strain No. 00211.

5 Claims, No Drawings

CLAVINE-PRODUCING STRAIN, A PROCESS FOR THE PREPARATION THEREOF AS WELL AS A MICROBIOLOGICAL PROCESS FOR PRODUCING CLAVINE ALKALOIDS

SPECIFICATION

Field of the Invention

The invention relates to a new microbiological process for the production of clavine alkaloids of the formula (I),

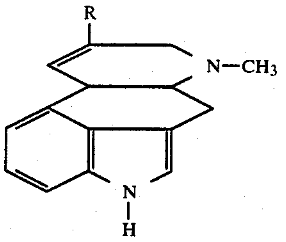

(I)

wherein

R stands for hydroxymethyl or methyl group, as well as to a biologically pure culture of the *Claviceps fusiformis* variant strain No. 00211 producing the said alkaloids, and to a process for obtaining and maintaining this biologically pure culture.

Of the alkaloids produced the elymoclavine (R=hydroxy-methyl) is of primary interest, being a pharmacon with analeptic and antiparkinsonian effects and inhibiting prolactin secretion [B. Berde and O. Schild: Ergot alkaloids and related compounds; Handb. Exp. Pharm., 49, Springer Verlag, Berlin (1978)]. Furthermore the elymoclavine is a possible starting material of the lysergol synthesis and an intermediate of Nicergoline. The agroclavine (R=methyl) is a precursor of the elymoclavine.

BACKGROUND OF THE INVENTION

It is known that Claviceps fungus strains are able to biosynthesize ergot alkaloids on rye in a host-parasite inter-relationship. About the clavine-producing Claviceps strains it was also known that they produce the alkaloids in question also under saprophytic conditions [M. Abe et al.: J. Agric. Chem. Soc. (Japan) 25, 458 (1952)]. While the latter way was not used for plant-scale manufacture, it provided an adequate basis for the research of the biosynthesis of the skeleton [L. C. Vining: Can. J. Microbiol. 12, 915 (1966) and H. G. Floss: Tetrahedron 32, 873 (1976)].

The first process used in industry was worked out by G. T. Banks et al. [J. Gen. Microbiol. 82, 345 (1974)]. In this process a *Claviceps fusiformis* strain was isolated from *Pennisetum typhoideum sclerotium* and then improved by repeated selection to obtain a higher yielding strain. The new strain produced agroclavine.

Then Z. Rehacek et al. prepared new mutants of the strain *Claviceps purpurea.* One mutant produced primarily agroclavine, while two other ones produced primarily elymoclavine. However, in the case of both elymoclavine-producing mutants the alkaloid level was only 300-600 μg/ml in the fermentation broth [J. Nat. Prod. 44, 225 (1981)].

The Soviet patent specification No. 735,010 as well as Prikl. Biok. Microbiol. 16, 569 (1980) disclose a native strain of *Claviceps fusiformis* producing six different alkaloids with a total alkaloid level of 1220 μg/ml, in which the elymoclavine portion amounts to 70-75%.

S. H. Ambiket et al. [Phytochem. 9, 1953-58 (1970)] have found that clavine-producing strains of the *Claviceps purpurea* type contain cytochrome P-450, and the level of the latter can be increased with phenobarbitone, resulting in a simultaneous increase of the alkaloid level produced by the strain.

OBJECT OF THE INVENTION

Our object was to obtain a strain capable of producing clavine alkaloids, primarily elymoclavine, in a high yield optionally together with alkaloids from which elymoclavine can easily be separated.

DESCRIPTION OF THE INVENTION

The model experiments were carried out with a strain of the *Claviceps fusiformis* type which, on a glycerin-peptone culture medium, produced agroclavine as a major alkaloid and elymoclavine as minor alkaloid [A. Tonolo and É. Unvardy-Nagy: Acta. Microbiol. Acad. Sci. Hung. 15, 29 (1968)]. This strain was deposited on May 2, 1977 at the National Collection of Microorganisms, National Institute for Public Health (Országos Közegészségügyi Intézet, Budapest) under No. 00164.

Investigations showed that this model strain contained an alternating oxidase enzyme, namely cytochrome P-450, and barbiturate additives stimulated both the cytochrome P-450 content and the total alkaloid production.

It has been found that when the culture of the 00164 strain was grown in the presence of barbiturates, the morphology and the pigmentation of the colonies became substantially different from those of the original ones. After repeated selection these new features became stable and were characteristic of the newly selected strain even in the absence of barbiturates.

The biochemical properties of the new variety differ from those of the parent strain, i.e. the strain No. 00164. The growth rate and the polysaccharide-forming ability are weaker while the alkaloid- and pigment-forming ability are stronger in the case of the new variety. What was really surprising is that the elymoclavine share in the total alkaloid level was predominant, whereas the parent strain produced primarily agroclavine.

This new strain was deposited on Oct. 15, 1981 at the National Collection of Microorganisms, National Institute for Public Health (Országos Közegészségügyi Inté zet, Budapest) under No. 00211.

Based on the above, the invention relates to a new microbiological process for the preparation of clavine alkaloids of the formula (I), wherein R stands for a methyl or a hydroxymethyl group, by cultivation of a *Claviceps fusiformis* strain in liquid submerged culture medium containing sources of carbon, nitrogen, mineral salts and optionally other additives, under aerobic conditions, in which a *Claviceps fusiformis* variant strain deposited under No. 00211 is used as alkaloid-producing strain and the alkaloids obtained are recovered.

The biologically pure culture of *Claviceps fusiformis* variant strain No. 00211, which can be fermented to produce clavine alkaloids of the formula (I) is also a feature of the invention.

The invention further relates to a process for the production of a biologically pure culture of *Claviceps fusiformis* variant strain No. 00211, in which a *Claviceps fusiformis* strain No. 00164 is cultured in a solid culture medium containing sources of carbon, nitrogen, mineral salts and agar as well as an additive promoting the formation of cytochrome P-450, followed by selective isolation of the new strain No. 00211.

The new strain is obtained in the presence of an additive promoting the formation of cytochrome P-450. Said additive is of the barbiturate type and is applied in an amount of 1 to 10 mmole/liter fermentation broth. The culture is incubated at 20°–28° C. for 7–21 days, and the violet colored, flatly outspread colonies of the new strain which are easy-to-distinguish from the parent strain colonies are selected, optionally the selection is repeated in or without the presence of barbiturates, and the new variant strain producing at least 85% elymoclavine is isolated.

According to the invention the parent strain No. 00164 is grown in a culture medium solidified with agar.

Culture mediums suitable for growing the parent strain have the following compositions.

Culture medium "A"

| | |
|---|---|
| saccharose | 100.0 g |
| l-asparagine | 10.0 g |
| calcium nitrate | 1.0 g |
| potassium dihydrogen phosphate | 0.25 g |
| magnesium sulfate | 0.25 g |
| potassium chloride | 0.125 g |
| ferrous sulfate | 0.033 g |
| zinc sulfate | 0.027 g |
| l-cysteine hydrochloride | 0.010 g |
| yeast extract (Difco) | 0.100 g |
| agar (Difco) | 30.0 g |

The pH of the solution of the above components is adjusted to 5.2 with sodium hydroxide, the liquid is diluted with water to 1000 ml and then sterilized at 110° C. for 30 minutes. Upon cooling the culture medium solidifies.

Culture medium "B"

From 39 g potato glucose agar (Difco) 1000 ml culture medium is prepared using the technique as described for medium "A".

Culture medium "C"

| | |
|---|---|
| saccharose | 100.0 g |
| succinic acid | 10.0 g |
| calcium nitrate | 1.0 g |
| ammonium nitrate | 1.0 g |
| potassium dihydrogen phosphate | 0.25 g |
| magnesium sulfate | 0.25 g |
| potassium chloride | 0.125 g |
| ferrous sulfate | 0.009 g |
| zinc sulfate | 0.003 g |
| agar (Difco) | 30.0 g |

The pH of the above mixture is adjusted to 5.5–5.6 with ammonium hydroxide and then 1 liter of culture medium is prepared as described for medium "A".

Culture medium "D"

| | |
|---|---|
| glycerin | 100 g |
| peptone (Difco) | 20 g |
| agar (Difco) | 30 g |

The above components are diluted with water to 1000 ml, the pH of the solution is adjusted to 6.5–6.8, then the solution is sterilized at 110° C. for 30 minutes.

Cultivation is carried out in any of the culture media listed above under sterile aerobic conditions at 20°–28° C. in the presence of an additive promoting formation of cytochrome P-450, preferably in the presence of barbiturates. As an additive of the barbiturate type N-phenylbarbiturates, e.g. phenobarbital or methylphenobarbital, can be taken into consideration. Cultivation is carried out for 7 to 21 days and then the colonies of the new strain are isolated. The new strain can be maintained on agar slant or in lyophilized form.

The main morphologic and biochemical features distinguishing the new strain from the parent one are shown in the following table.

| Morphologic and biochemical features | Strain No. 00164 | Strain No. 00211 |
|---|---|---|
| Colony morphology in culture medium "C" on the 21st day | Beige colored, sharp-edged colonies with wrinkled surface 10–15 mm in diameter | Violet colored, sharp-edged, flat colonies with aerial-mycelium 15–20 mm in diameter |
| Colony morphology in culture medium "C" on the 12th day (submerged culture) (a) macroscopic characteristics | Beige colored, dense, viscous culture | Brownish-violet colored, thin flocculent culture. |
| (b) Microscopic characteristics | long hyphae, 3–6μ in diameter, frequently forming threads | |
| Phenobarbital tolerance | | |
| (a) in solid (agar) culture medium | 1 mmole/liter | 10 mmoles/liter |
| (b) in liquid culture medium | 0.6 mmole/liter | 5 mmoles/liter |
| Cytochrome P-450 level (nmole/g dry mycelial cell) in culture medium "C", during the 4–7th day | 1.0–1.5 | 2.5–3.0 |
| Polysaccharide level (mg/ml) on the 7th day in culture medium "C" | 20.8 | 3.8 |
| Total alkaloid production rate (μg/ml/day) on the 4–7th day in culture medium "C" (prepared without agar) | 50–80 | 200–250 |
| Alkaloid content | | |
| (a) in culture medium "C" (prepared without agar) | | |
| agroclavine % | 75–80 | 5–15 |
| elymoclavine % | 20–25 | 85–95 |
| (b) in culture medium "D" (prepared without agar) | | |
| agroclavine % | 90–95 | 5–10 |
| elymoclavine % | 5–10 | 90–95 |

The new strain No. 00211 disclosed above is applicable for the preparation of clavine alkaloids in the following manner:

In the fermentation process a suitable liquid culture medium containing sources of carbon, nitrogen, mineral salts and optionally other additives is used. In the alkaloid-producing fermentation among others the following culture medium compositions are applicable:

Culture medium "E"

| | |
|---|---|
| mannitol | 40.0 g/liter |

-continued

| | |
|---|---|
| succinic acid | 10.0 g/liter |
| corn steep liquor | 2.0 g/liter |
| potassium dihydrogen phosphate | 1.0 g/liter |
| magnesium sulfate | 0.3 g/liter |

The pH of the solution of the above components is adjusted to 5.2–5.3 with ammonium hydroxide.

Culture medium "F"

| | |
|---|---|
| saccharose | 50.0 g/liter |
| grated potatoes | 10.0 g/liter |
| ammonium nitrate | 1.0 g/liter |
| potassium dihydrogen phosphate | 0.25 g/liter |
| magnesium sulfate | 0.25 g/liter |

The pH of the solution of the above components is adjusted to 5.4–5.5 with ammonium hydroxide.

Culture medium "G"

| | |
|---|---|
| sorbitol | 60.0 g/liter |
| succinic acid | 36.0 g/liter |
| potassium dihydrogen phosphate | 0.25 g/liter |
| magnesium sulfate | 0.30 g/liter |
| ferrous sulfate | 0.009 g/liter |
| zinc sulfate | 0.003 g/liter |

The pH of the solution of the above components is adjusted to 5.4–5.5 with ammonium hydroxide.

Any composition listed above is dissolved in water at 50°–60° C. and sterilized at 110° C. for 30 minutes.

Culture media "E", "F" and "G" as described above or culture media "C" or "D" prepared without agar are suitable for alkaloid production. The fermentation is carried out under sterile, aerobic conditions in submerged culture at 20°–28° C. for 10–15 days in a pH range of 4.2 to 6.0.

The invention is elucidated in detail by the aid of the following non-limiting Examples.

EXAMPLE 1

14-day old colonies of *Claviceps fusiformis* variant strain No. 00211 grown on culture medium "A" were removed from the agar surface with 5 ml of physiological saline. The resulting suspension was homogenized and 1 ml inoculum was transferred to a 500-ml Erlenmeyer flask containing 100 ml of medium "C" prepared without agar. The culture was incubated at 24° C. for 7 days on a rotary shaker (240 r.p.m., 2 cm displacement).

4 ml of the resulting culture was transferred to a 500-ml Erlenmeyer flask containing 100 ml of presterilized medium "C". The culture was grown for 12 days under the above conditions. On the 3rd and 5th days 1-1 ml of 10% sterile aqueous solution of yeast extract (Difco) were added to the fermentation broth.

On the 12th day the dry mycelial cell content of the broth was 18 g/liter. The beige-violet coloured mycelial mat was separated from the medium and the total alkaloid content of the filtrate, determined by van Urk's reagent using elymoclavine standard, was 1300 μg/ml.

The elymoclavine and agroclavine content of the broth was determined as follows: 20 ml of the homogenized culture was extracted with 40 ml of a 4:1 mixture of chloroform and isopropanol at pH 9. 10 ml of the organic layer was evaporated to dryness under reduced pressure. The residue was dissolved in 0.5 ml of a 1:1 mixture of chloroform and methanol. 20 μl of the solution was subjected to TLC using DC Alufolien Kieselgel $60F_{254}$ (Merck, Art. 5554) adsorbent and a 4:1 mixture of chloroform-ethanol as developing agent. Spots were detected at 254 nm by UV light. The elymoclavine (Rf 0.20) and the agroclavine (Rf 0.30) were determined by spectrophotometry at 283 nm in a 1:1 mixture of methanol and tartaric acid. The elymoclavine content was 1150 μg/ml, the agroclavine level was 55 μg/ml.

EXAMPLE 2

Lyophilized colonies of *Claviceps fusiformis* variant strain No. 00211 were suspended in 2 ml of physiological saline. The homogenized suspension was transferred to a 500-ml Erlenmeyer flask containing 100 ml of pre-sterilized medium "E". The culture was grown for 7 days under the conditions described in Example 1.

2×2 mls of the resulting culture were transferred to 500-ml Erlenmeyer-flasks both containing 100 ml of medium "G". The cultures were grown at 24° C. under shaking for 3 days. The resulting inocula were transferred to a 10-liter glass-fermenter containing 5 l of sterile culture medium "G". The cultures were grown at 24° C. under aeration (0.5 l/l/min.) and stirring (430 r.p.m.) for 12 days. If necessary, 0.5 ml/l of sterile Struktol SB 2020 antifoam agent was added.

At the end of the fermentation the broth contained 16 g of dry mycelial cell/liter and the total alkaloid content determined according to Example 1 was 1550 μg/ml, from which the elymoclavine amounted to 1435 μg/ml and the agroclavine to 90 μg/ml.

EXAMPLE 3

Lyophilized colonies of *Claviceps fusiformis* variant strain No. 00211 were suspended in 2 ml of physiological saline and the homogenized suspension was inoculated on medium "B". The culture was incubated at 24° C. in the dark for 14 days. The seed culture so obtained was removed from the surface and homogenized with 5 ml of physiological saline. 2×2 ml of the homogenized culture were transferred to 500-ml Erlenmeyer flasks containing 100 ml of medium "F", each. The cultures were shaken at 24° C. for 5 days and then transferred to a 10-l glass-fermenter containing 5 liters of sterile culture medium "C".

The culture was grown at 24° C. under aeration (0.5 l/l/min.) and stirring (430 r.p.m.) for two days. The inoculum so obtained was transferred into a 160 l stainless steel fermenter containing 110 l of sterile medium C supplemented with 20 g/l of sodium chloride.

The culture was grown at 24° C. under aeration (0.4 l/l/min.) and stirring (200 r.p.m.) for 12 days. During the fermentation procedure sterile Struktol SB 2020 antifoam agent was added in a total amount of about 220 ml.

The finished fermentation broth contained 15 g of dry mycelial cell/liter, and 1815μ total alkaloid/ml from which the elymoclavine amounted to 1630 μg/ml and the agroclavine to 240 μg/ml. The broth was filtered and in the filtrate the elymoclavine and agroclavine were determined by HPLC (adsorbent: Nucleosil 10 C 18; eluant: 3:2 mixture of acetonitrile and 0.01M aqueous ammonium carbonate; UV detection at 280 nm). The elymoclavine appeared with a retention time of 8.7 minutes, the agroclavine with that of 32.0 minutes.

What we claim is:

1. A microbiological process for the preparation of clavine alkaloids of the Formula (I)

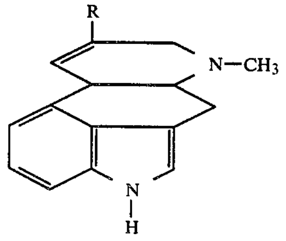

(I)

wherein R stands for a methyl or a hydroxymethyl group, by culturing a *Claviceps fusiformia* strain in a liquid submerged culture medium containing sources of carbon, nitrogen, and mineral salts, under aerobic conditions, which comprises using a *Claviceps fusiformia* variant strain deposited under No. 00211 as alkaloid producing strain on Nov. 15, 1981 at the National Collection of Microorganisms, National Institute for Public Health, Budapest, Hungary, and recovering the alkaloids obtained.

2. The process as claimed in claim 1, in which the fermentation is performed at a temperature of 20° to 28° C. in a pH range of 4.2 to 6.0.

3. A biologically pure culture of *Claviceps fusiformis* variant strain No. 00211 which was deposited on Nov. 15, 1981 at the National Collection of Microorganisms, National Institute for Public Health, Budapest, Hungary, and which can be fermented to produce clavine alkaloids of the Formula (I)

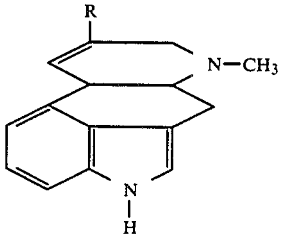

(I)

wherein R stands for a methyl or a hydroxymethyl group.

4. A process for the preparation of a biologically pure culture of *Claviceps fusiformis* variant strain No. 00211, deposited on Nov. 15, 1981 at the National Collection of Microorganism, National Institute for Public Health, Budapest, Hungary, which comprises the step of culturing the *Claviceps fusiformis* strain No. 00164, deposited on May 2, 1977 at the National Collection of Microorganisms, National Institute for Public Health, Budapest, Hungary, in a solid culture medium containing sources of carbon, nitrogen, mineral salts, and agar as well as a barbiturate additive promoting the formation of cytochrome P-450, and isolating the colonies of the new strain No. 00211 by selection.

5. A process as claimed in claim 4 in which the barbiturate is used in an amount of 1 to 10 mmoles/liter of fermentation broth.

* * * * *